United States Patent
Durant et al.

(10) Patent No.: US 8,182,418 B2
(45) Date of Patent: May 22, 2012

(54) SYSTEMS AND METHODS FOR ARTICULATING AN ELONGATE BODY

(75) Inventors: Kevin Durant, San Francisco, CA (US); Joshua Oen, Fremont, CA (US); David Mintz, Mountain View, CA (US); Keith Phillip Laby, San Francisco, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 1123 days.

(21) Appl. No.: 12/036,976

(22) Filed: Feb. 25, 2008

(65) Prior Publication Data

US 2009/0216083 A1  Aug. 27, 2009

(51) Int. Cl.
 A61B 1/00 (2006.01)
 B25J 17/00 (2006.01)
 B25J 17/02 (2006.01)
 B25J 18/00 (2006.01)

(52) U.S. Cl. ............ 600/142; 600/141; 74/490.05

(58) Field of Classification Search .. 74/490.01–490.05; 606/1, 205–209
See application file for complete search history.

(56) References Cited

U.S. PATENT DOCUMENTS

| | | |
|---|---|---|
| 616,672 A | 12/1898 | Kelling |
| 2,510,198 A | 6/1950 | Tesmer |
| 2,533,494 A | 12/1950 | Mitchell, Jr. |
| 2,767,705 A | 10/1956 | Moore |
| 3,060,972 A | 10/1962 | Sheldon |
| 3,071,161 A | 1/1963 | Ulrich |
| 3,096,962 A | 7/1963 | Meijs |
| 3,162,214 A | 12/1964 | Bazinet, Jr. |
| 3,168,274 A | 2/1965 | Street |
| 3,190,286 A | 6/1965 | Stokes |
| 3,266,059 A | 8/1966 | Stelle |
| 3,430,662 A | 3/1969 | Guarnaschelli |
| 3,497,083 A | 2/1970 | Anderson |
| 3,546,961 A | 12/1970 | Marton |
| 3,557,780 A * | 1/1971 | Sato ........................ 600/141 |
| 3,610,231 A | 10/1971 | Takahashi |
| 3,625,084 A | 12/1971 | Low |
| 3,643,653 A | 2/1972 | Takahashi et al. |
| 3,739,770 A | 6/1973 | Mori |
| 3,773,034 A | 11/1973 | Burns et al. |
| 3,780,740 A | 12/1973 | Rhea |
| 3,858,578 A | 1/1975 | Milo |
| 3,871,358 A | 3/1975 | Fukuda et al. |
| 3,897,775 A | 8/1975 | Furihata |
| 3,913,565 A | 10/1975 | Kawahara |
| 3,946,727 A | 3/1976 | Okada |

(Continued)

FOREIGN PATENT DOCUMENTS

DE  2823025  12/1979

(Continued)

OTHER PUBLICATIONS

Belson et al; U.S. Appl. No. 11/796,220 entitled "Steerable segmented endoscope and method of insertion," filed Apr. 27, 2007.

(Continued)

*Primary Examiner* — Matthew J Kasztejna
*Assistant Examiner* — Ryan Henderson (57) ABSTRACT

Systems and methods for articulating an elongate articulatable body which is adapted to be delivered within a body cavity. Particularly, systems and methods for enhancing an articulating force on the elongate body without increasing an actuation force applied by an actuator.

22 Claims, 8 Drawing Sheets

U.S. PATENT DOCUMENTS

| | | |
|---|---|---|
| 3,990,434 A | 11/1976 | Free |
| 4,054,128 A | 10/1977 | Seufert |
| 4,176,662 A | 12/1979 | Frazer |
| 4,233,981 A | 11/1980 | Schomacher |
| 4,236,509 A | 12/1980 | Takahashi |
| 4,240,435 A | 12/1980 | Yazawa et al. |
| 4,273,111 A | 6/1981 | Tsukaya |
| 4,327,711 A | 5/1982 | Takagi |
| 4,366,810 A | 1/1983 | Slanetz, Jr. |
| 4,393,728 A | 7/1983 | Larson |
| 4,432,349 A | 2/1984 | Oshiro |
| 4,483,326 A | 11/1984 | Yamaka et al. |
| 4,489,826 A | 12/1984 | Dubson |
| 4,494,417 A | 1/1985 | Larson |
| 4,499,895 A | 2/1985 | Takayama |
| 4,503,842 A | 3/1985 | Takayama |
| 4,543,090 A | 9/1985 | McCoy |
| 4,551,061 A | 11/1985 | Olenick |
| 4,559,928 A | 12/1985 | Takayama |
| 4,566,843 A * | 1/1986 | Iwatsuka et al. ............... 414/680 |
| 4,577,621 A | 3/1986 | Patel |
| 4,592,341 A | 6/1986 | Omagari et al. |
| 4,601,283 A | 7/1986 | Chikama |
| 4,601,713 A | 7/1986 | Fuqua |
| 4,621,618 A | 11/1986 | Omagari |
| 4,624,243 A | 11/1986 | Lowery et al. |
| 4,630,649 A | 12/1986 | Oku |
| 4,643,184 A | 2/1987 | Mobin-Uddin |
| 4,646,722 A | 3/1987 | Silverstein et al. |
| 4,648,733 A | 3/1987 | Merkt |
| 4,651,718 A | 3/1987 | Collins et al. |
| 4,655,257 A | 4/1987 | Iwashita |
| 4,683,773 A | 8/1987 | Diamond |
| 4,686,963 A | 8/1987 | Cohen et al. |
| 4,712,969 A | 12/1987 | Kimura |
| 4,726,355 A | 2/1988 | Okada |
| 4,753,222 A | 6/1988 | Morishita |
| 4,753,223 A | 6/1988 | Bremer |
| 4,754,909 A | 7/1988 | Barker et al. |
| 4,784,117 A | 11/1988 | Miyazaki |
| 4,787,369 A | 11/1988 | Allred, III |
| 4,788,967 A | 12/1988 | Ueda |
| 4,793,326 A | 12/1988 | Shishido |
| 4,796,607 A | 1/1989 | Allred, III |
| 4,799,474 A | 1/1989 | Ueda |
| 4,800,890 A | 1/1989 | Cramer |
| 4,807,593 A | 2/1989 | Ito |
| 4,815,450 A | 3/1989 | Patel |
| 4,832,473 A | 5/1989 | Ueda |
| 4,834,068 A | 5/1989 | Gottesman |
| 4,873,965 A | 10/1989 | Danieli |
| 4,873,990 A | 10/1989 | Holmes et al. |
| 4,879,991 A | 11/1989 | Ogiu |
| 4,884,557 A | 12/1989 | Takehana et al. |
| 4,890,602 A | 1/1990 | Hake |
| 4,895,431 A | 1/1990 | Tsujiuchi et al. |
| 4,899,731 A | 2/1990 | Takayama et al. |
| 4,904,048 A | 2/1990 | Sogawa et al. |
| 4,917,114 A | 4/1990 | Green et al. |
| 4,919,112 A | 4/1990 | Siegmund |
| 4,930,494 A | 6/1990 | Takehana et al. |
| 4,949,927 A | 8/1990 | Madocks et al. |
| 4,957,486 A | 9/1990 | Davis |
| 4,969,709 A | 11/1990 | Sogawa et al. |
| 4,971,035 A | 11/1990 | Ito |
| 4,977,886 A | 12/1990 | Takehana et al. |
| 4,977,887 A | 12/1990 | Gouda |
| 4,987,314 A | 1/1991 | Gotanda et al. |
| 5,005,558 A | 4/1991 | Aomori |
| 5,005,559 A | 4/1991 | Blanco et al. |
| 5,014,709 A | 5/1991 | Bjelkhagen et al. |
| 5,018,509 A | 5/1991 | Suzuki et al. |
| 5,025,778 A | 6/1991 | Silverstein et al. |
| 5,025,804 A * | 6/1991 | Kondo ........................ 600/146 |
| 5,060,632 A | 10/1991 | Hibino et al. |
| 5,092,901 A | 3/1992 | Hunter et al. |
| 5,125,395 A | 6/1992 | Adair |
| 5,127,393 A | 7/1992 | McFarlin et al. |
| 5,159,446 A | 10/1992 | Hibino et al. |
| 5,166,787 A | 11/1992 | Irion |
| 5,174,276 A | 12/1992 | Crockard |
| 5,174,277 A | 12/1992 | Matsumaru |
| 5,188,111 A | 2/1993 | Yates et al. |
| 5,207,695 A | 5/1993 | Trout, III |
| 5,217,001 A | 6/1993 | Nakao et al. |
| 5,220,911 A | 6/1993 | Tamura |
| 5,228,429 A | 7/1993 | Hatano |
| 5,234,448 A | 8/1993 | Wholey et al. |
| 5,243,967 A | 9/1993 | Hibino |
| 5,250,058 A | 10/1993 | Miller et al. |
| 5,251,611 A | 10/1993 | Zehel et al. |
| 5,253,647 A | 10/1993 | Takahashi |
| 5,254,809 A | 10/1993 | Martin |
| 5,257,617 A | 11/1993 | Takahashi |
| 5,259,364 A | 11/1993 | Bob et al. |
| 5,271,381 A | 12/1993 | Ailinger et al. |
| 5,271,382 A | 12/1993 | Chikama |
| 5,279,610 A | 1/1994 | Park et al. |
| 5,297,443 A | 3/1994 | Wentz |
| 5,325,845 A | 7/1994 | Adair |
| 5,337,732 A | 8/1994 | Grundfest et al. |
| 5,337,733 A | 8/1994 | Bauerfeind |
| 5,343,874 A | 9/1994 | Picha |
| 5,347,987 A | 9/1994 | Feldstein et al. |
| 5,348,259 A | 9/1994 | Blanco et al. |
| 5,370,108 A | 12/1994 | Miura et al. |
| 5,383,467 A | 1/1995 | Auer et al. |
| 5,383,852 A | 1/1995 | Stevens-Wright |
| 5,389,222 A | 2/1995 | Shahinpoor |
| 5,394,864 A | 3/1995 | Kobayashi et al. |
| 5,400,769 A | 3/1995 | Tanii et al. |
| 5,402,768 A | 4/1995 | Adair |
| 5,411,508 A | 5/1995 | Bessler et al. |
| 5,413,108 A | 5/1995 | Alfano |
| 5,421,337 A | 6/1995 | Richards-Kortum et al. |
| 5,425,738 A | 6/1995 | Gustafson et al. |
| 5,429,118 A | 7/1995 | Cole et al. |
| 5,439,000 A | 8/1995 | Gunderson et al. |
| 5,451,221 A | 9/1995 | Cho et al. |
| 5,456,714 A | 10/1995 | Owen |
| 5,460,166 A | 10/1995 | Yabe et al. |
| 5,460,168 A | 10/1995 | Masubuchi et al. |
| 5,469,840 A | 11/1995 | Tanii et al. |
| 5,482,029 A | 1/1996 | Sekiguchi et al. |
| 5,487,757 A | 1/1996 | Truckai et al. |
| 5,489,256 A | 2/1996 | Adair |
| 5,507,287 A | 4/1996 | Palcic et al. |
| 5,507,717 A | 4/1996 | Kura et al. |
| 5,531,664 A | 7/1996 | Adachi et al. |
| 5,551,945 A | 9/1996 | Yabe et al. |
| 5,558,619 A | 9/1996 | Kami et al. |
| 5,558,665 A | 9/1996 | Kieturakis |
| 5,577,992 A | 11/1996 | Chiba et al. |
| 5,586,968 A | 12/1996 | Grundl et al. |
| 5,590,660 A | 1/1997 | MacAulay et al. |
| 5,601,087 A | 2/1997 | Gunderson et al. |
| 5,602,449 A | 2/1997 | Krause |
| 5,620,408 A | 4/1997 | Vennes et al. |
| 5,624,380 A | 4/1997 | Takayama et al. |
| 5,624,381 A | 4/1997 | Kieturakis |
| 5,626,553 A | 5/1997 | Frassica et al. |
| 5,645,520 A | 7/1997 | Nakamura et al. |
| 5,647,368 A | 7/1997 | Zeng et al. |
| 5,651,769 A | 7/1997 | Waxman et al. |
| 5,653,690 A | 8/1997 | Booth et al. |
| 5,658,238 A | 8/1997 | Suzuki et al. |
| 5,662,585 A | 9/1997 | Willis et al. |
| 5,662,587 A | 9/1997 | Grundfest et al. |
| 5,665,050 A | 9/1997 | Benecke |
| 5,667,476 A | 9/1997 | Frassica et al. |
| 5,679,216 A | 10/1997 | Takayama et al. |
| 5,728,044 A | 3/1998 | Shan |
| 5,733,245 A | 3/1998 | Kawano |
| 5,749,828 A | 5/1998 | Solomon et al. |
| 5,752,912 A | 5/1998 | Takahashi et al. |
| 5,759,151 A | 6/1998 | Sturges |
| 5,762,613 A | 6/1998 | Sutton et al. |

| | | | |
|---|---|---|---|
| 5,765,561 A | 6/1998 | Chen et al. | |
| 5,769,792 A | 6/1998 | Palcic et al. | |
| 5,772,597 A | 6/1998 | Goldberg | |
| 5,773,835 A | 6/1998 | Sinofsky | |
| 5,779,624 A | 7/1998 | Chang | |
| 5,807,241 A | 9/1998 | Heimberger | |
| 5,810,715 A | 9/1998 | Moriyama | |
| 5,810,716 A | 9/1998 | Mukherjee | |
| 5,810,717 A | 9/1998 | Maeda | |
| 5,810,776 A | 9/1998 | Bacich et al. | |
| 5,813,976 A | 9/1998 | Filipi et al. | |
| 5,827,190 A | 10/1998 | Palcic et al. | |
| 5,842,973 A | 12/1998 | Bullard | |
| 5,860,581 A | 1/1999 | Robertson et al. | |
| 5,860,914 A | 1/1999 | Chiba et al. | |
| 5,876,329 A | 3/1999 | Harhen | |
| 5,876,373 A | 3/1999 | Giba et al. | |
| 5,885,208 A | 3/1999 | Moriyama | |
| 5,893,369 A | 4/1999 | LeMole | |
| 5,897,417 A | 4/1999 | Grey | |
| 5,897,488 A | 4/1999 | Ueda | |
| 5,902,254 A | 5/1999 | Magram | |
| 5,906,591 A | 5/1999 | Dario et al. | |
| 5,908,381 A | 6/1999 | Aznoian et al. | |
| 5,912,147 A | 6/1999 | Boury | |
| 5,916,147 A | 6/1999 | Boury | |
| 5,921,915 A | 7/1999 | Aznoian et al. | |
| 5,928,136 A | 7/1999 | Barry | |
| 5,941,815 A | 8/1999 | Chang | |
| 5,941,908 A | 8/1999 | Goldsteen et al. | |
| 5,957,833 A | 9/1999 | Shan | |
| 5,968,052 A | 10/1999 | Sullivan et al. | |
| 5,971,767 A | 10/1999 | Kaufman et al. | |
| 5,976,074 A | 11/1999 | Moriyama | |
| 5,989,182 A | 11/1999 | Hori et al. | |
| 5,989,230 A | 11/1999 | Frassica | |
| 5,993,381 A | 11/1999 | Ito | |
| 5,993,447 A | 11/1999 | Blewett et al. | |
| 5,996,346 A | 12/1999 | Maynard | |
| 6,013,024 A * | 1/2000 | Mitsuda et al. | 600/146 |
| 6,016,440 A | 1/2000 | Simon et al. | |
| 6,033,359 A | 3/2000 | Doi | |
| 6,036,636 A | 3/2000 | Motoki et al. | |
| 6,042,155 A | 3/2000 | Lockwood | |
| 6,048,307 A | 4/2000 | Grundl et al. | |
| 6,063,022 A | 5/2000 | Ben-Haim | |
| 6,066,102 A | 5/2000 | Townsend et al. | |
| 6,066,132 A | 5/2000 | Chen et al. | |
| 6,068,638 A | 5/2000 | Makower | |
| 6,096,289 A | 8/2000 | Goldenberg | |
| 6,099,464 A | 8/2000 | Shimizu et al. | |
| 6,099,465 A | 8/2000 | Inoue | |
| 6,099,485 A | 8/2000 | Patterson | |
| 6,106,510 A | 8/2000 | Lunn et al. | |
| 6,119,913 A | 9/2000 | Adams et al. | |
| 6,129,667 A | 10/2000 | Dumoulin et al. | |
| 6,129,683 A | 10/2000 | Sutton et al. | |
| 6,141,577 A | 10/2000 | Roland | |
| 6,149,581 A | 11/2000 | Klingenstein | |
| 6,162,171 A | 12/2000 | Ng et al. | |
| 6,174,280 B1 | 1/2001 | Oneda | |
| 6,174,291 B1 | 1/2001 | McMahon et al. | |
| 6,179,776 B1 | 1/2001 | Adams | |
| 6,185,448 B1 | 2/2001 | Borovsky | |
| 6,201,989 B1 | 3/2001 | Whitehead | |
| 6,203,493 B1 | 3/2001 | Ben-Haim | |
| 6,203,494 B1 | 3/2001 | Moriyama | |
| 6,210,337 B1 | 4/2001 | Dunham et al. | |
| 6,221,006 B1 | 4/2001 | Dubrul et al. | |
| 6,241,657 B1 | 6/2001 | Chen et al. | |
| 6,249,076 B1 | 6/2001 | Madden et al. | |
| 6,270,453 B1 | 8/2001 | Sakai | |
| 6,306,081 B1 | 10/2001 | Ishikawa et al. | |
| 6,309,346 B1 | 10/2001 | Farhadi | |
| 6,315,714 B1 | 11/2001 | Akiba | |
| 6,319,197 B1 | 11/2001 | Tsuji et al. | |
| 6,327,492 B1 | 12/2001 | Lemelson | |
| 6,332,089 B1 | 12/2001 | Acker | |
| 6,348,058 B1 | 2/2002 | Melkent | |
| 6,366,799 B1 | 4/2002 | Acker | |
| 6,402,687 B1 | 6/2002 | Ouchi | |
| 6,408,889 B1 | 6/2002 | Komachi | |
| 6,428,203 B1 | 8/2002 | Danley | |
| 6,443,888 B1 | 9/2002 | Ogura et al. | |
| 6,453,190 B1 | 9/2002 | Acker | |
| 6,459,481 B1 | 10/2002 | Schaack | |
| 6,468,203 B2 | 10/2002 | Belson | |
| 6,482,149 B1 | 11/2002 | Torii | |
| 6,485,413 B1 | 11/2002 | Boppart | |
| 6,490,467 B1 | 12/2002 | Bucholz | |
| 6,511,417 B1 | 1/2003 | Taniguchi et al. | |
| 6,511,418 B2 | 1/2003 | Shahidi | |
| 6,517,477 B1 | 2/2003 | Wendlandt | |
| 6,527,706 B2 | 3/2003 | Ide | |
| 6,537,211 B1 | 3/2003 | Wang et al. | |
| 6,544,215 B1 | 4/2003 | Bencini et al. | |
| 6,554,793 B1 | 4/2003 | Pauker et al. | |
| 6,569,173 B1 | 5/2003 | Blatter et al. | |
| 6,616,600 B2 | 9/2003 | Pauker | |
| 6,638,213 B2 | 10/2003 | Ogura et al. | |
| 6,641,528 B2 | 11/2003 | Torii | |
| 6,656,110 B1 | 12/2003 | Irion et al. | |
| 6,699,183 B1 | 3/2004 | Wimmer | |
| 6,761,685 B2 | 7/2004 | Adams et al. | |
| 6,783,491 B2 | 8/2004 | Saadat et al. | |
| 6,790,173 B2 | 9/2004 | Saadat et al. | |
| 6,800,056 B2 | 10/2004 | Tartaglia et al. | |
| 6,808,499 B1 | 10/2004 | Churchill et al. | |
| 6,808,520 B1 | 10/2004 | Fourkas et al. | |
| 6,817,973 B2 | 11/2004 | Merril et al. | |
| 6,817,974 B2 * | 11/2004 | Cooper et al. | 600/142 |
| 6,837,846 B2 | 1/2005 | Jaffe | |
| 6,837,847 B2 | 1/2005 | Ewers et al. | |
| 6,837,849 B2 | 1/2005 | Ogura et al. | |
| 6,843,793 B2 | 1/2005 | Brock et al. | |
| 6,850,794 B2 | 2/2005 | Shahidi | |
| 6,858,005 B2 | 2/2005 | Ohline | |
| 6,869,396 B2 | 3/2005 | Belson | |
| 6,875,170 B2 | 4/2005 | Francois et al. | |
| 6,890,297 B2 | 5/2005 | Belson | |
| 6,902,528 B1 | 6/2005 | Garibaldi et al. | |
| 6,942,613 B2 | 9/2005 | Ewers et al. | |
| 6,960,161 B2 | 11/2005 | Amling et al. | |
| 6,960,162 B2 | 11/2005 | Saadat et al. | |
| 6,960,163 B2 | 11/2005 | Ewers et al. | |
| 6,974,411 B2 | 12/2005 | Belson | |
| 6,984,203 B2 | 1/2006 | Tartaglia et al. | |
| 7,018,331 B2 | 3/2006 | Chang et al. | |
| 7,087,013 B2 | 8/2006 | Belson et al. | |
| 7,662,091 B2 * | 2/2010 | Bagley et al. | 600/146 |
| 7,758,569 B2 * | 7/2010 | Brock | 606/1 |
| 2002/0016607 A1 | 2/2002 | Bonadio et al. | |
| 2002/0062062 A1 | 5/2002 | Belson et al. | |
| 2002/1012025 | 8/2002 | Julian | |
| 2002/0147385 A1 | 10/2002 | Butler et al. | |
| 2002/0151767 A1 | 10/2002 | Sonnenschein | |
| 2002/0169361 A1 | 11/2002 | Taniguchi | |
| 2002/0193662 A1 | 12/2002 | Belson | |
| 2003/0083550 A1 | 5/2003 | Miyagi | |
| 2003/0130598 A1 | 7/2003 | Manning et al. | |
| 2003/0167007 A1 | 9/2003 | Belson | |
| 2003/0182091 A1 | 9/2003 | Kukuk | |
| 2003/0195387 A1 | 10/2003 | Kortenbach et al. | |
| 2003/0233056 A1 | 12/2003 | Saadat et al. | |
| 2003/0236505 A1 | 12/2003 | Bonadio et al. | |
| 2003/0236549 A1 | 12/2003 | Bonadio et al. | |
| 2004/0019254 A1 | 1/2004 | Belson | |
| 2004/0044270 A1 | 3/2004 | Barry | |
| 2004/0049251 A1 | 3/2004 | Knowlton | |
| 2004/0097788 A1 | 5/2004 | Mourlas et al. | |
| 2004/0106852 A1 | 6/2004 | Windheuser et al. | |
| 2004/0176683 A1 | 9/2004 | Whitin et al. | |
| 2004/0186350 A1 | 9/2004 | Brenneman et al. | |
| 2004/0193008 A1 | 9/2004 | Jaffe et al. | |
| 2004/0193009 A1 | 9/2004 | Jaffe et al. | |
| 2004/0210109 A1 | 10/2004 | Jaffe et al. | |
| 2004/0220450 A1 | 11/2004 | Jaffe et al. | |
| 2004/0230096 A1 | 11/2004 | Stefanchik et al. | |

| | | | |
|---|---|---|---|
| 2005/0020901 A1 | 1/2005 | Belson et al. | |
| 2005/0085693 A1 | 4/2005 | Belson et al. | |
| 2005/0124855 A1 | 6/2005 | Jaffe et al. | |
| 2005/0137454 A1 | 6/2005 | Saadat et al. | |
| 2005/0137455 A1 | 6/2005 | Ewers et al. | |
| 2005/0137456 A1 | 6/2005 | Saadat et al. | |
| 2005/0154258 A1 | 7/2005 | Tartaglia et al. | |
| 2005/0154261 A1 | 7/2005 | Ohline et al. | |
| 2005/0165276 A1 | 7/2005 | Belson | |
| 2005/0168571 A1 | 8/2005 | Lia et al. | |
| 2005/0203339 A1 | 9/2005 | Butler et al. | |
| 2005/0209506 A1 | 9/2005 | Butler et al. | |
| 2005/0209509 A1 | 9/2005 | Belson | |
| 2005/0222497 A1 | 10/2005 | Belson | |
| 2005/0222498 A1 | 10/2005 | Belson | |
| 2005/0250990 A1 | 11/2005 | Le et al. | |
| 2006/0009678 A1 | 1/2006 | Jaffe et al. | |
| 2006/0025652 A1* | 2/2006 | Vargas | 600/114 |
| 2006/0052664 A1 | 3/2006 | Julian et al. | |
| 2006/0199999 A1* | 9/2006 | Ikeda et al. | 600/141 |
| 2006/0235457 A1 | 10/2006 | Belson | |
| 2006/0235458 A1 | 10/2006 | Belson | |
| 2006/0258912 A1 | 11/2006 | Belson et al. | |
| 2007/0043259 A1 | 2/2007 | Jaffe et al. | |
| 2007/0093858 A1 | 4/2007 | Belson et al. | |
| 2007/0135803 A1 | 6/2007 | Belson | |
| 2007/0161291 A1 | 7/2007 | Swinehart et al. | |
| 2007/0161857 A1 | 7/2007 | Durant et al. | |
| 2007/0249901 A1 | 10/2007 | Ohline et al. | |
| 2007/0270650 A1 | 11/2007 | Eno et al. | |
| 2008/0154288 A1 | 6/2008 | Belson | |

FOREIGN PATENT DOCUMENTS

| | | |
|---|---|---|
| DE | 3707787 | 9/1988 |
| DE | 4102211 A1 | 8/1991 |
| DE | 19626433 A1 | 1/1998 |
| DE | 19729499 A1 | 1/1999 |
| EP | 0165718 A2 | 12/1985 |
| EP | 0382974 A1 | 8/1990 |
| EP | 0497781 B1 | 1/1994 |
| EP | 0993804 A1 | 4/2000 |
| EP | 1101442 A2 | 5/2001 |
| EP | 1681013 A1 | 7/2006 |
| FR | 2732225 A1 | 10/1996 |
| GB | 2347685 A | 9/2000 |
| IE | 2000/0225 | 3/2000 |
| IE | 2000/0559 | 7/2000 |
| IE | 2002/0170 | 3/2002 |
| JP | 63-136014 | 6/1988 |
| JP | 63-272322 | 11/1988 |
| JP | 01-152413 | 6/1989 |
| JP | 01-229220 | 9/1989 |
| JP | 01-262372 | 10/1989 |
| JP | 02-246986 | 10/1990 |
| JP | 02-296209 | 12/1990 |
| JP | 03-136630 | 6/1991 |
| JP | 04-054970 | 2/1992 |
| JP | 05-011196 | 1/1993 |
| JP | 05-111458 | 5/1993 |
| JP | 05-305073 | 11/1993 |
| JP | 06-007287 | 1/1994 |
| JP | 08-322786 | 12/1996 |
| JP | 09-028662 | 2/1997 |
| JP | 10-337274 | 12/1998 |
| JP | 11-042258 | 2/1999 |
| JP | 2001-046318 | 2/2001 |
| SU | 871786 | 10/1981 |
| SU | 1256955 | 9/1986 |
| SU | 1301701 | 4/1987 |
| WO | WO 93/17751 A1 | 9/1993 |
| WO | WO 94/19051 A1 | 9/1994 |
| WO | WO 95/04556 A2 | 2/1995 |
| WO | WO 95/09562 A1 | 4/1995 |
| WO | WO 96/05768 A1 | 2/1996 |
| WO | WO 97/10746 A1 | 3/1997 |
| WO | WO 97/25101 A2 | 7/1997 |
| WO | WO 97/29701 A1 | 8/1997 |
| WO | WO 97/29710 A1 | 8/1997 |
| WO | WO 98/24017 A2 | 6/1998 |
| WO | WO 98/49938 A1 | 11/1998 |
| WO | WO 99/16359 A1 | 4/1999 |
| WO | WO 99/33392 A1 | 7/1999 |
| WO | WO 99/51283 A2 | 10/1999 |
| WO | WO 99/59664 A1 | 11/1999 |
| WO | WO 00/10456 A1 | 3/2000 |
| WO | WO 00/27462 A1 | 5/2000 |
| WO | WO 00/54653 A1 | 9/2000 |
| WO | WO 00/74565 A1 | 12/2000 |
| WO | WO 01/49353 A2 | 7/2001 |
| WO | WO 01/67964 A2 | 9/2001 |
| WO | WO 01/70096 A1 | 9/2001 |
| WO | WO 01/70097 A1 | 9/2001 |
| WO | WO 01/74235 A1 | 10/2001 |
| WO | WO 01/80935 A1 | 11/2001 |
| WO | WO 02/24058 A2 | 3/2002 |
| WO | WO 02/39909 A1 | 5/2002 |
| WO | WO 02/47549 A1 | 6/2002 |
| WO | WO 02/064028 A1 | 8/2002 |
| WO | WO 02/068988 A1 | 9/2002 |
| WO | WO 02/069841 A2 | 9/2002 |
| WO | WO 02/089692 A1 | 11/2002 |
| WO | WO 02/096276 A1 | 12/2002 |
| WO | WO 03/028547 A2 | 4/2003 |
| WO | WO 03/073920 A2 | 9/2003 |
| WO | WO 03/073921 A1 | 9/2003 |
| WO | WO 03/092476 A2 | 11/2003 |
| WO | WO 2004/006980 A2 | 1/2004 |
| WO | WO 2004/019769 A1 | 3/2004 |
| WO | WO 2004/049905 A2 | 6/2004 |
| WO | WO 2004/071284 A1 | 8/2004 |
| WO | WO 2004/080313 A1 | 9/2004 |
| WO | WO 2004/084702 A1 | 10/2004 |
| WO | WO 2005/084542 A1 | 9/2005 |
| WO | WO 2006/134881 | 12/2006 |

OTHER PUBLICATIONS

Woodley et al; U.S. Appl. No. 11/871,104 entitled "System for managing bowden cables in articulating instruments," filed Oct. 11, 2007.

Berger, W. L. et al. "Sigmoid Stiffener for Decompression Tube Placement in Colonic Pseudo-Obstruction." Endoscopy. 2000; 32 (1): 54-57.

Hasson, H.M. "Technique of open laparoscopy:equipment and technique. (from step 1 to step 9)." May 1979, 2424 North Clark Street, Chicago, IL 60614. 3 pages.

Lee, et al. "A highly redundant robot system for inspection." Proceedings of Conference on Intelligent Robotics in Field, Factory, Service, and Space (CIRFFSS "94). Mar. 21-24, 1994. 1:142-148. Houston, Texas.

McKernan, et al. "Laparoscopic general surgery." Journal of the Medical Association of Georgia. 1990; 79 (3):157-159.

Science & Technology, Laptop Magazine. Oct. 2002. p. 98.

Slatkin, et al. "The development of a robotic endoscope." Proceedings 1995 IEEE/RSJ International Conference on Intelligent Robots and Systems. Aug. 5-9, 1995. 2:162-171. Pittsburgh, Pennsylvania.

PCT/US09/35097 International Search Report and Written Opinion, mailed Apr. 13, 2009, 8 pages.

* cited by examiner

SYSTEMS AND METHODS FOR ARTICULATING AN ELONGATE BODY

INCORPORATION BY REFERENCE

All publications and patent applications mentioned in this specification are incorporated herein, in their entirety, by reference to the same extent as if each individual publication or patent application was specifically and individually indicated to be incorporated by reference.

BACKGROUND OF THE INVENTION

The forms of robots vary widely, but all robots share the features of a mechanical, movable structure under some form of control. The mechanical structure or kinematic chain (analogous to the human skeleton) of a robot is formed from several links (analogous to human bones), actuators (analogous to human muscle) and joints permitting one or more degrees of freedom of motion of the links. A continuum or multi-segment robot is a continuously curving device, like an elephant trunk for example. An example of a continuum or multi-segment robot is a snake-like endoscopic device, like that under investigation by NeoGuide Systems, Inc., and described in U.S. Pat. Nos. 6,468,203; 6,610,007; 6,800,056; 6,974,411; 6,984,203; 6,837,846; and 6,858,005. Another example of a snake-like robotic device is shown and described in U.S. Patent Publication US2005/0059960 to Simaan, et al.

Snake-like robots transfer forces from an actuator to particular sections or segments of the snake-like robot to effect articulation of that section or segment. The amount of articulating force that is ultimately applied to the section or segment can be less than the actuation force applied by an actuator in the robotic system. This can be due to, for example, frictional losses between system components. In robotic systems with many moveable parts that may be in very close proximity to one another, those losses can be magnified. Thus, a system is needed that can enhance the amount of force applied to articulate a segment or section of a robotic system (i.e., an articulating force) without increasing the amount of force applied by an actuator in the system (i.e., an actuation force).

SUMMARY OF THE INVENTION

The present invention relates generally to systems and methods for articulating an elongate articulatable body which is adapted to be delivered within a body cavity. Particularly, the invention relates to systems and methods for enhancing an articulating force on the elongate body without increasing an actuation force that is applied by an actuator.

One aspect of the invention is a system for modifying (e.g., enhancing) an articulating force on an articulatable elongate body deliverable within a body cavity. The system includes an elongate body comprising at least one articulatable segment, wherein the at least one articulatable segment comprises a plurality of links and at least one force modifying element. The system also includes a coil pipe within the elongate body which has a proximal end terminated outside of the elongate body and a distal end terminated at a proximal portion of the segment. The system also includes a tendon disposed at least partially within the coil pipe, the tendon having a proximal end and a distal end, where the proximal end is coupled to an actuator outside of the elongate body, the distal end is coupled to a link proximal to the force modifying element, and the tendon interacts with the force modifying element.

In some embodiments the force modifying element is disposed at a distal portion of the segment and the distal end of the tendon is coupled to a proximal portion of the segment.

In some embodiments the coil pipe and the distal end of the tendon are coupled to the same link.

In some embodiments the at least one segment comprises a plurality of force modifying elements, and wherein the system comprises a plurality of tendons each coupled at their proximal ends to the actuator. The plurality of tendons can be at least three tendons and the plurality of force modifying elements can be at least three force modifying elements. In some embodiments two of the at least three force modifying elements are coupled to a first link, and at least the third force enhancing element is coupled to a second link adjacent the first link.

The force modifying element can comprise a curved surface and the tendon and force modifying element can slidingly interact. The curved surface can be a fixed curve surface such that the tendon loops around and slides over the curved surface when actuated, or alternatively the curved surface can be adapted to move, such as, for example and without limitation, a pulley.

In some embodiments, the plurality of links are adapted such that when an actuation force is applied to the segment at least one link does not become locked in position relative to an adjacent link. In these embodiments the segment can therefore continue to articulate, or bend, as additional actuation, or tensioning, forces are applied to the segment. Although articulation of the segment may cause a link to come into contact with an adjacent link or to be temporarily fixed in place relative to an adjacent link, the links are adapted to be able to continue to move relative to one another (i.e., the segment can continue to be articulated) as additional tensioning forces are applied to articulate the segment.

One aspect of the invention is a method of modifying an articulating force on an elongate body deliverable within a body cavity. The method includes inserting an elongate articulatable instrument into a body cavity, extending a tendon along the length of the elongate articulatable instrument, wherein the elongate articulatable instrument comprises a force modifying element in a distal region of the elongate articulatable instrument, and wherein the tendon interacts with the force enhancing element. The method also includes articulating the elongate articulatable instrument by applying a tensioning force on the tendon with an actuator coupled to the proximal end of the tendon, thereby generating an articulation force in the distal region of the elongate articulatable instrument that is larger than the tensioning force. In one embodiment of this method, the elongate articulatable instrument comprises multiple segments, and at least one of the segments has the force modifying element that engages with the tendon.

BRIEF DESCRIPTION OF THE DRAWINGS

The novel features of the invention are set forth with particularity in the claims that follow. A better understanding of the features and advantages of the present invention will be obtained by reference to the detailed description below that sets forth illustrative embodiments, in which the principles of the invention are utilized, and the accompanying drawings.

In the drawings.

DETAILED DESCRIPTION OF THE INVENTION

Figure 1:
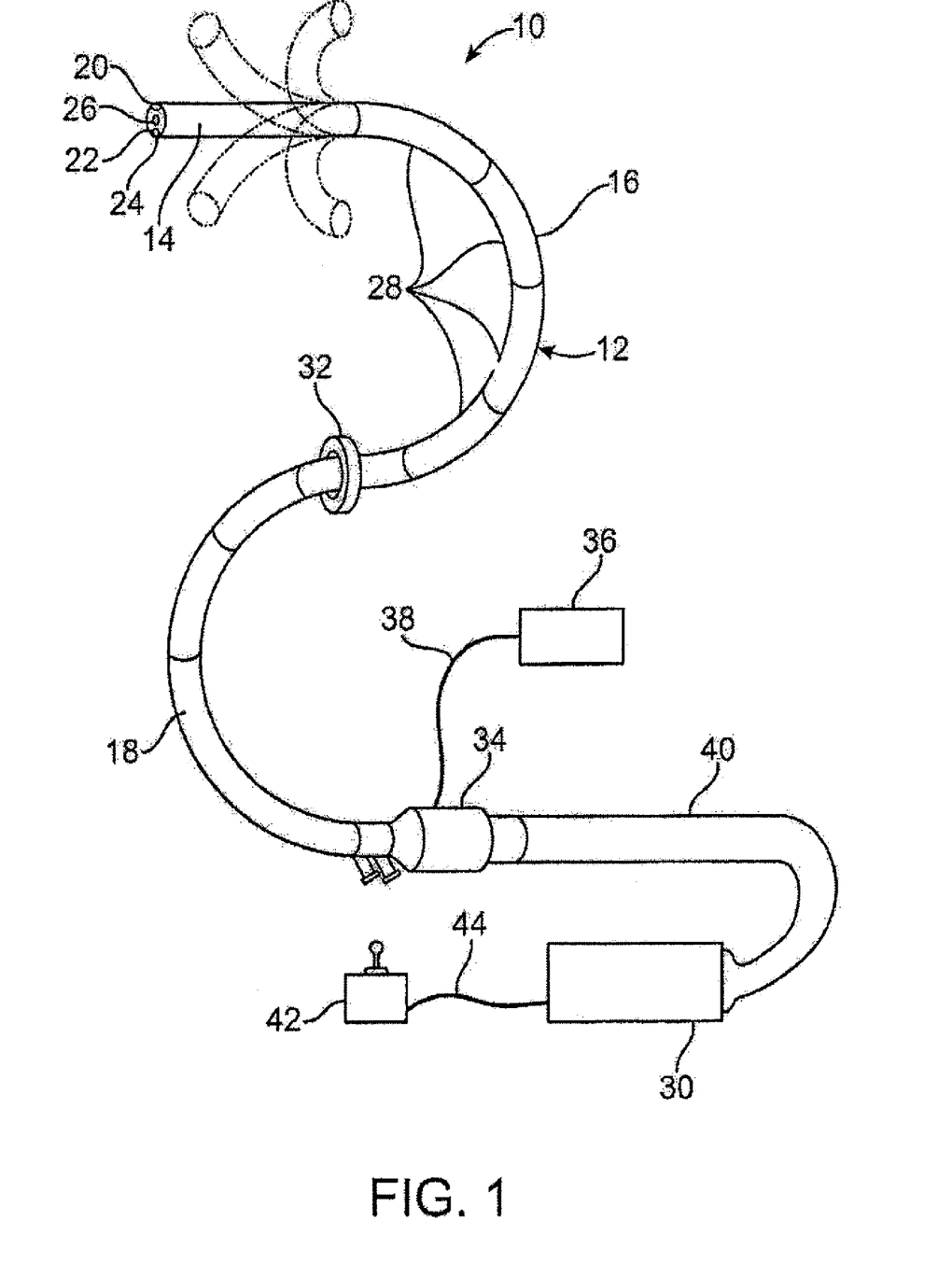
FIG. 1 illustrates an exemplary system in accordance with an embodiment of the present invention.

FIG. 1 illustrates an exemplary system into which the present invention can be incorporated. Endoscope 10 has elongate body 12 with steerable distal portion 14, automatically controlled proximal portion 16, and flexible and passively manipulated proximal portion 18. The skilled artisan will appreciate that automatically controlled proximal portion 16 may also be flexible and passively manipulated, although it is preferred to provide automatically controlled proximal portion 16. The skilled artisan will also appreciate that elongate body 12 can have only steerable distal portion 14 and automatically controlled portion 16. Fiber optic imaging bundle 20 (or other imaging system) and illumination fiber(s) 22 may extend through elongate body 12 to steerable distal portion 14, or video camera 24 (e.g., CCD or CMOS camera) may be positioned at the distal end of steerable distal portion 14. Generally, a user views live or delayed video feed from video camera 24 via a video cable (e.g., wire or optical fiber, not shown) or through wireless transmission of the video signal. Endoscope 10 will typically also include one or more access lumens, working channels, light channels, air and water channels, vacuum channels, and a host of other well known complements useful for both medical and industrial endoscopy. These channels and other amenities are shown generically as 26, because such channels and amenities are well known in the art.

Preferably, system 10 comprises a plurality of articulatable segments 28 (which includes steerable distal portion 14), which are controlled via computer and/or electronic controller 30. Such an exemplary automatically controlled endoscope is described in further detail in commonly assigned U.S. patent application Ser. No. 10/229,577 (now U.S. Pat. No. 6,858,00) and Ser. No. 11/750,988, both previously incorporated herein by reference. Preferably, the distal end of a tendon (more thoroughly described below) is mechanically connected to each articulatable segment 28, while the proximal end of the tendon is mechanically connected to an actuator which is used to articulate segments 28 and/or steerable distal portion 14. This is more fully described below and in U.S. patent application Ser. No. 10/229,577 (now U.S. Pat. No. 6,858,005) and Ser. No. 11/750,988, both incorporated by reference herein.

The actuators driving the tendons may include a variety of different types of mechanisms capable of applying a force to a tendon, e.g., electromechanical motors, pneumatic and hydraulic cylinders, pneumatic and hydraulic motors, solenoids, shape memory alloy wires, electronic rotary actuators or other devices or methods as known in the art. If shape memory alloy wires are used, they are preferably configured into several wire bundles attached at a proximal end of each of the tendons within the controller. Segment articulation may be accomplished by applying energy, e.g., electrical current, electrical voltage, heat, etc., to each of the bundles to actuate a linear motion in the wire bundles which in turn actuate the tendon movement. The linear translation of the actuators within the controller may be configured to move over a relatively short distance to accomplish effective articulation depending upon the desired degree of segment movement and articulation. In addition, the skilled artisan will also appreciate that knobs attached to rack and pinion gearing can be used to actuate the tendons attached to steerable distal portion 14. Axial motion transducer 32 (also called a depth referencing device or datum) may be provided for measuring the axial motion, i.e., the depth change, of elongate body 12 as it is advanced and withdrawn. As elongate body 12 of endoscope 10 slides through axial motion transducer 32, it indicates the axial position of the elongate body 12 with respect to a fixed point of reference. Axial motion transducer 32 is more fully described in U.S. patent application Ser. No. 10/229,577, which is incorporated herein by reference.

In the embodiment depicted in FIG. 1, handle 34 is connected to illumination source 36 by illumination cable 38 that is connected to or continuous with illumination fibers 22. Handle 34 is connected to electronic controller 30 by way of controller cable 40. Steering controller 42 (e.g., a joy stick) is connected to electronic controller 30 by way of second cable 44 or directly to handle 34. Electronic controller 30 controls the movement of the segmented automatically controlled proximal portion 16, which is described more thoroughly below and in U.S. patent application Ser. No. 11/750,988, previously incorporated herein by reference.

Figure 2:
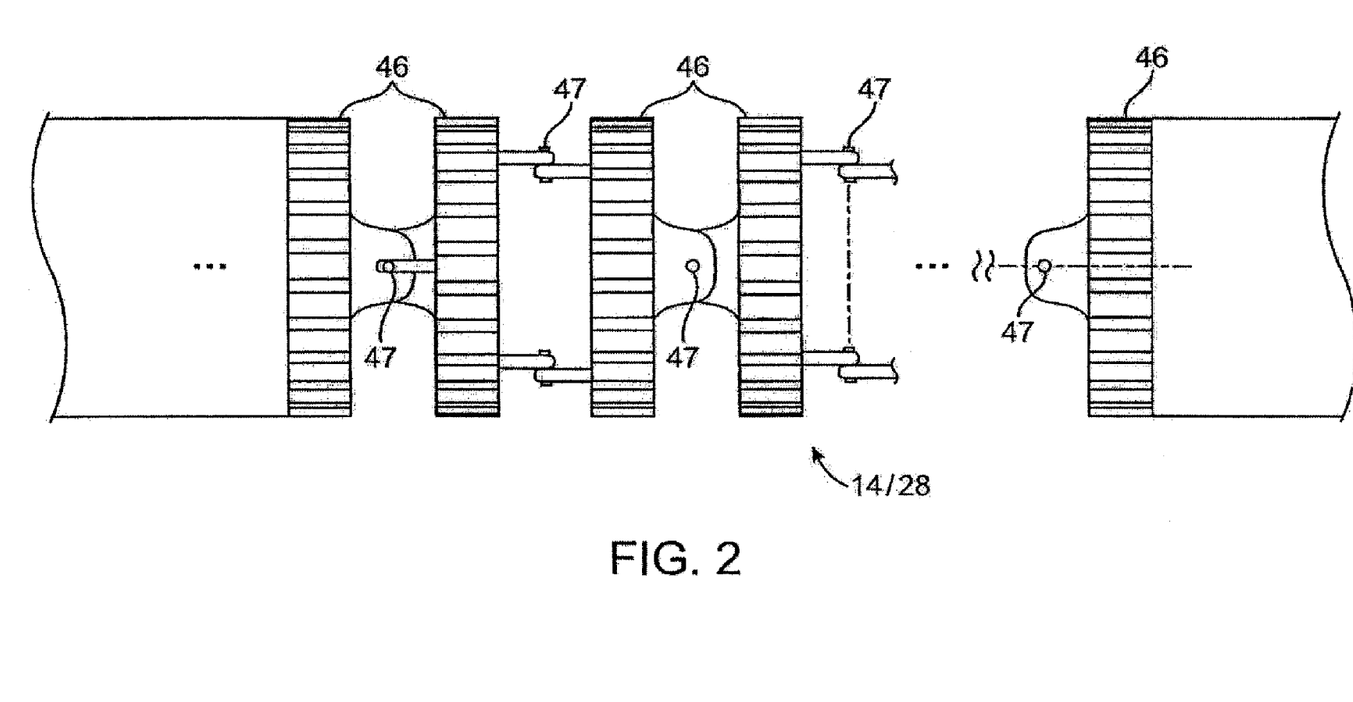
FIG. 2 illustrates an exemplary articulatable segment including a plurality of links.

FIG. 2 illustrates a portion of an exemplary articulatable segment 28 preferably constructed from a plurality of links 46. It will be appreciated that a segment may be comprised of a single link or a plurality of links. Five links 46 are shown for the sake of clarity, although the skilled artisan will recognize that any number of links may be used, the ultimate number being primarily defined by the purpose for which the articulatable segment 28 or steerable distal portion 14 will be used. Each link 46 connects one joint 47 to an adjacent joint 47. Each link 46, in this embodiment, can move (at the joints) with one degree of freedom relative to an adjacent link.

Figure 3A:
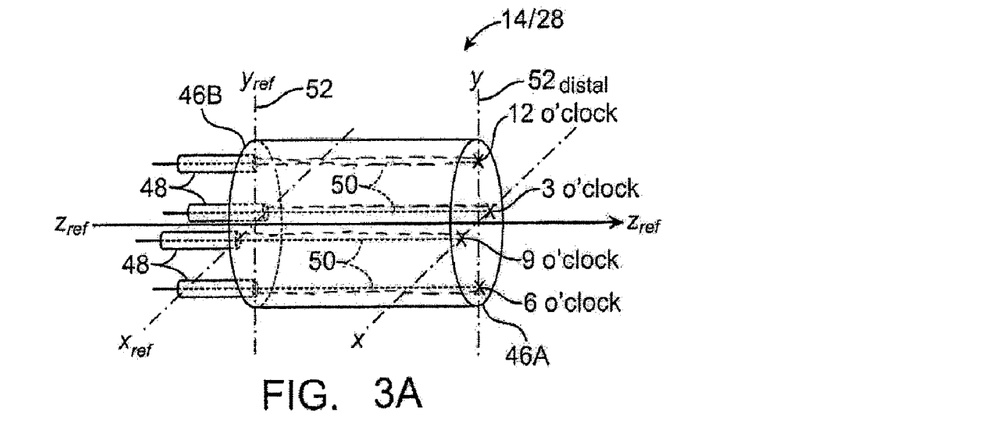
FIGS. 3A-3C illustrate a schematic diagram of an articulatable segment in accordance with the present invention.
Figure 3B:
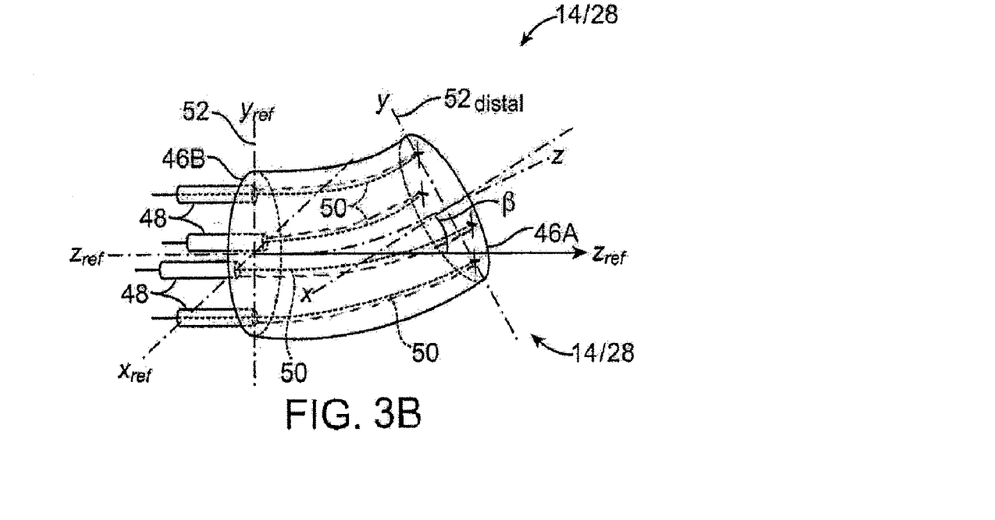
Figure 3C:
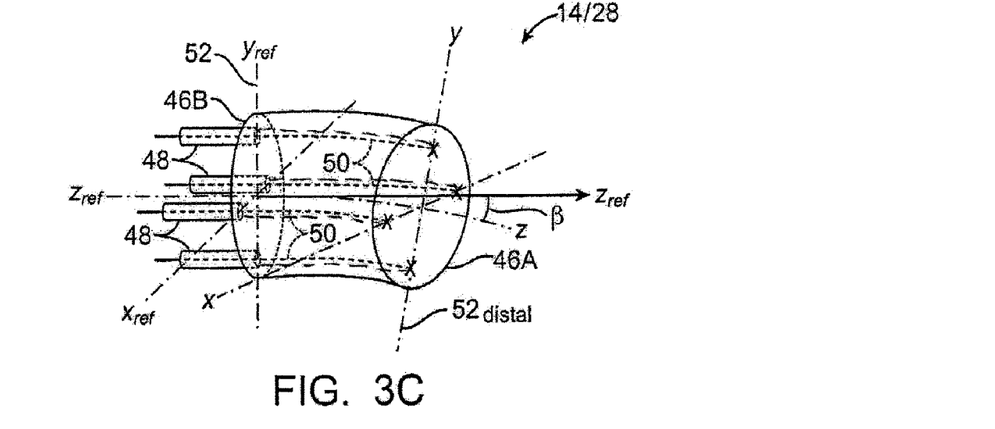

Referring now to FIG. 3A-C, simplified schematic diagrams of segments 28 according to the invention are provided for discussion purposes and to explain a preferred system and method for articulating segments 28. The skilled artisan will recognize that the system and method for articulation is the same for both steerable distal portion 14 and segments 28 of automatically controlled proximal portion 16. Therefore, the system and method for articulation will be described referring only to segments 28, with the recognition that the description also applies equally to steerable distal portion 14. It is noted that details relating to links 46, joints 47 and the interconnections of the links have been eliminated from this figure for the sake of clarity.

FIG. 3A shows a three-dimensional view of segment 28 in its substantially straight configuration. The most distal link 46A and most proximal link 46B are depicted as circles. Cables extend down the length of elongate body 12 (not shown in FIG. 3A-C) and comprise coil pipes 48 and tendons 50. The proximal end of the tendon 50 is coupled to an actuator (not shown) and the distal end is coupled to the most proximal link 46B. Coil pipes 48 house tendons 50 (i.e. a Bowden-type cable) along the length of elongate body 12 (not shown in FIG. 3A-C) and coil pipes 48 are fixed at (or near) the proximal end of segment 28. Tendons 50 extend out of coil pipes 48 at or near the proximal end of segment 28 along the length of segment 28, interact with force modifying elements located at or near the distal end of segment 28 (not shown but described below), and the distal ends of tendons are mechanically attached to segment 28 at a point proximal to the distal end of segment 28, and preferably at or near the proximal end of segment 28.

In FIGS. 3A-C, four tendons 50 are depicted to articulate segment 28, but more or fewer may be used. The coil pipe/ tendon combination, or Bowden cables, can be used to apply force to articulate segments 28 and can be actuated remotely to deliver forces as desired to articulate segments 28. In this manner, actuation of one or more tendons 50 causes segment 28 to articulate. In the embodiment depicted, links 46 have joints 47 offset by 90 degrees (see FIGS. 2 and 4). Thus, an articulatable segment is able to move in many directions, limited only by the number and position of joints. As will be appreciated by the skilled artisan, tendons 50 can be made from a variety of materials, which is primarily dictated by the purpose for which the system will be used. Without limitation, tendons 50 can be made from stainless steel, titanium, nitinol, ultra high molecular weight polyethylene, the latter of which is preferred, or any other suitable material known to the skilled artisan.

Four tendons can reliably articulate segment 28 in many directions. The distal ends of tendons 50 are shown attached to the most proximal link near the periphery spaced equally apart. They are shown positioned at 12, 3, 6, and 9 o'clock. If more or fewer are used, the tendons can remain equally spaced around the periphery of the segment. For example, if three tendons are used, they can be positioned at the 12, 4, and 8 o'clock positions. Alternatively, if only two are used, they can be positioned at the 12 and 6 o'clock positions.

FIGS. 3B-C show segment 28 articulated by independently pulling or slacking at least one of the four tendons 50. For example, referring to FIG. 3B, pulling on tendon 50 at the 12 o'clock position and easing tension on tendon 50 at the 6 o'clock position causes steerable distal portion 28 to articulate in the positive y-direction with respect to the z-y-x reference frame 52. It is noted that the most distal z-y-x coordinate frame $52_{distal}$ rotates with respect to the z-y-x reference frame 52 and that β is the degree of overall articulation of segment 28. In this situation β is only along the positive y-axis, up, because only tendon 50 at the 12 o'clock position was pulled while easing tension or giving slack to tendon 50 at 6 o'clock. The tendons 50 at 3 and 9 o'clock were left substantially static in this example, and, thus, had approximately no or little affect on articulation of segment 28. The reverse situation (not depicted), pulling on tendon 50 at the 6 o'clock position and slacking or easing the tension on tendon 50 at the 12 o'clock position results in articulation of segment 28 in the negative y-direction, or down. Referring to FIG. 3C the same logic applies to articulate segment 28 in the positive x-direction (right) or a negative x-direction (left, not shown). Segment 28 can be articulated in any direction by applying varying tensions to the tendons off axis, e.g., applying tension to the tendons at 12 o'clock and 3 o'clock results in an articulation up and to the left.

Referring now to FIG. 4, links 46 may be control rings to provide the structure needed to construct segments 28. FIG. 4A shows a first variation of a vertebra-type control ring 54. FIG. 4B shows an end view of a single vertebra-type control ring 54 of this first variation. In this embodiment the vertebra-type control ring 54 defines a central aperture 56 that collectively form an internal lumen of the segment, which internal lumen is used to house the various access lumens, working channels, light channels, air and water channels, vacuum channels, and any other known complements useful for both medical and industrial endoscopy. Vertebrae-type control rings 54 have two pairs of joints or hinges 58A and 58B; the first pair 58A projecting perpendicularly from a first face of the vertebra and a second pair 58B, located 90 degrees around the circumference from the first pair, projecting perpendicularly away from the face of the vertebra on a second face of the vertebra opposite to the first face. Hinges 58A and 58B are tab-shaped, however other shapes may also be used.

Figure 4B:
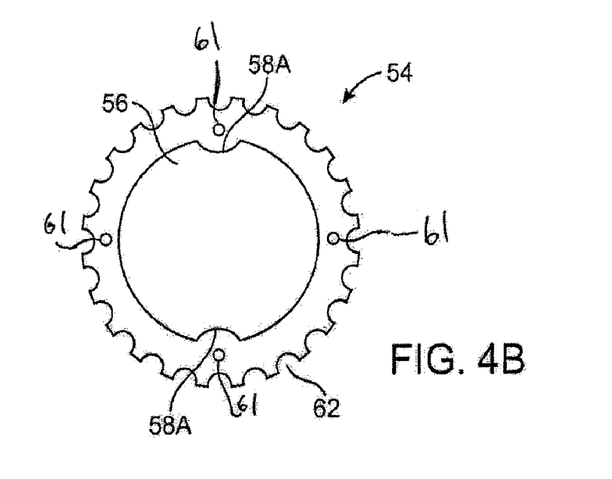
Figure 4C:
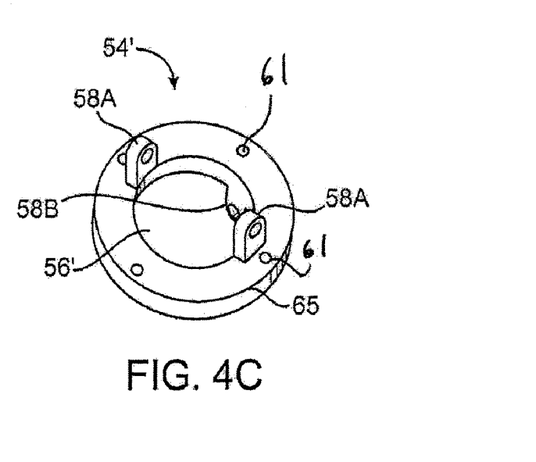
Figure 5:
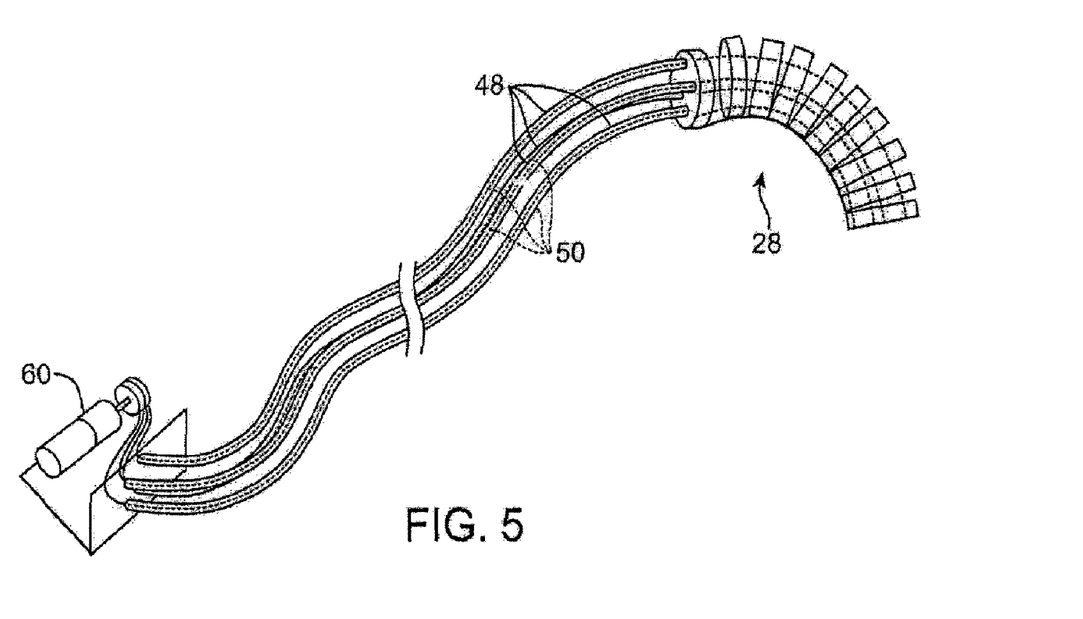
FIG. 5 illustrates a schematic of an exemplary system showing relative positions of actuators, coil pipes, tendons, and an articulatable segment.

Referring briefly to FIG. 5, tension applied to a tendon 50 by actuator 60 is isolated to a particular segment 28 by use of coil pipes 48 which house tendons 50, as previously described. While not shown in FIG. 5 for sake of clarity, it is understood that the tendons extend from coil pipes 48 to the distal end of the segment 28 (at which point the tendons engage a force modifying element, described in more detail below), then extend proximally to a location proximal to the distal end where they are attached. Referring to FIG. 4B, control ring 54 is shown with four holes 61 through the edge of control ring 54 that may act as, e.g., attachment sites for tendon 50, as a throughway for tendon 50 in other vertebrae-type control rings 54 (links) of that particular segment 28, and/or attachment sites for coil pipes 48 when vertebra-type control ring 54 is the most proximal link in segment 28. The skilled artisan will appreciate that the number of tendons 50 used to articulate each segment 28 determines the number of holes 61 provided for passage of tendons 50. When hole 61 is used as an attachment site for a coil pipe and the distal end of the tendon 50 is also attached to control ring 54 (after engaging with force modifying element), the distal end of tendon 50 can simply be attached to the most proximal link with almost any type of attachment mechanism, e.g., adhesive, tying, or there may be an additional hole or rod close to hole 61 to which the tendon can be tied.

Figure 4A:
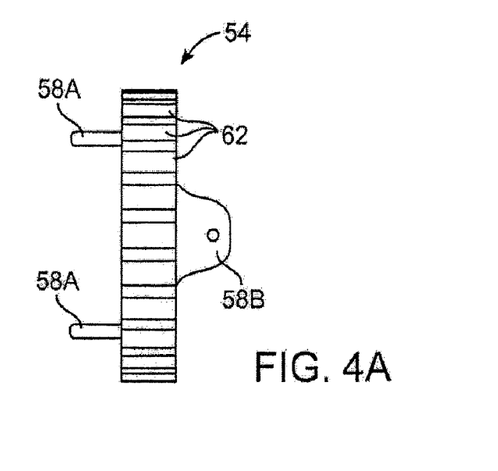
FIGS. 4A-4E illustrate embodiments of vertebrae-type control rings in accordance with embodiments of the present invention.

The outer edge of vertebra-type control ring 54 in the variation depicted in FIGS. 4A-B may be scalloped to provide bypass spaces 62 for tendons 50 and coil pipes 48 that control more distal segments 28 that bypass vertebra-type control ring 54 and the present segment 28. These coil pipe bypass spaces 62, in this variation of the vertebrae-type control ring 54, preferably conform to the outer diameter of coil pipes 48. The number of coil pipe bypass spaces 62 vary depending on the number of tendons, and, therefore, the number of coil pipes needed to articulate all the segments 28 and steerable distal portion 14. It will be appreciated that not all vertebrae-type control rings 54 of a particular segment 28 need to have coil pipe bypass spaces 62. As described further below, intermediate vertebra-type control rings 54' (FIG. 4C) between segments need not have coil pipe bypass spaces 62, rather the coil pipes can simply pass through the lumen formed by central aperture 56'. In this alternative, the lumen formed by central aperture 56' house the various access lumens, working channels, light channels, air and water channels, vacuum channels, as described above, as well as coil pipe/tendon combinations that do not control that particular segment.

Figure 4D:
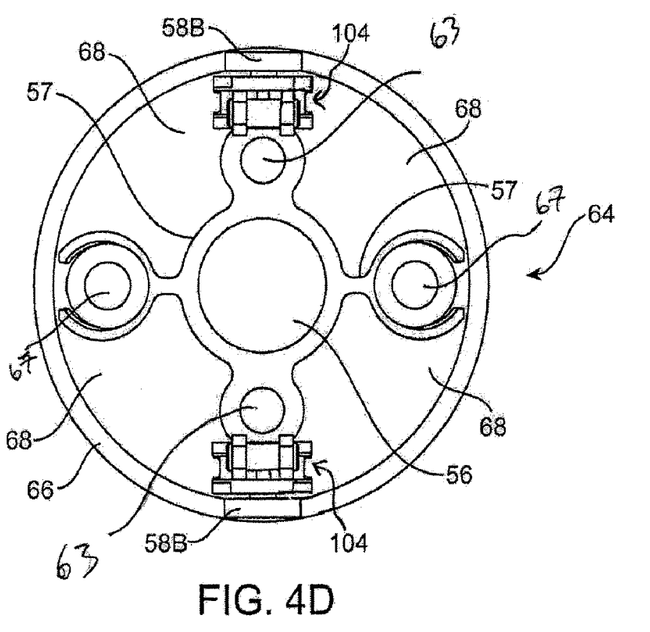
Figure 4E:
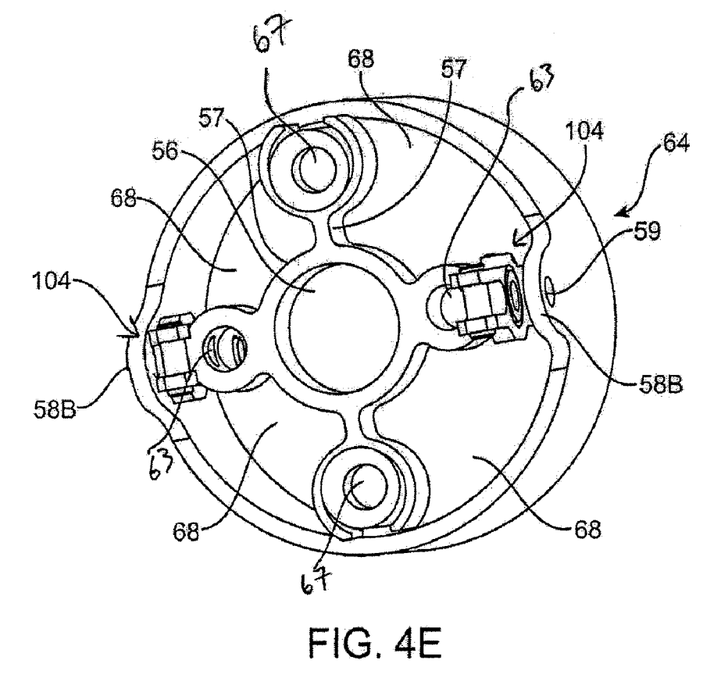

FIGS. 4D-E show an exemplary control ring 64 in sectional and perspective proximal views (i.e., looking in the distal direction) and a segment can comprise one or more of these links.

Control ring 64 comprises body 66, which is hingedly coupled to inner cross bar member 57 at joints 59. Joints 59 are the same joints at which a second link (although not shown) adjacent and proximal to link 64 is hingedly coupled to link 64. Inner cross bar member 57 is therefore hingedly coupled to two links at joints 59, and can be thought of as being axially disposed "between" the two links. Cross bar member 57 can also be fixed relative to one or both of the adjacent links. The exemplary inner cross bar member 57 comprises force modifying elements 104 which each interact with a tendon 50 (not shown in FIGS. 4D and 4E) to increase the amount of force applied to the articulatable segment when an actuation/tensioning force is applied to the tendon (e.g., through an actuator).

Figure 4F:
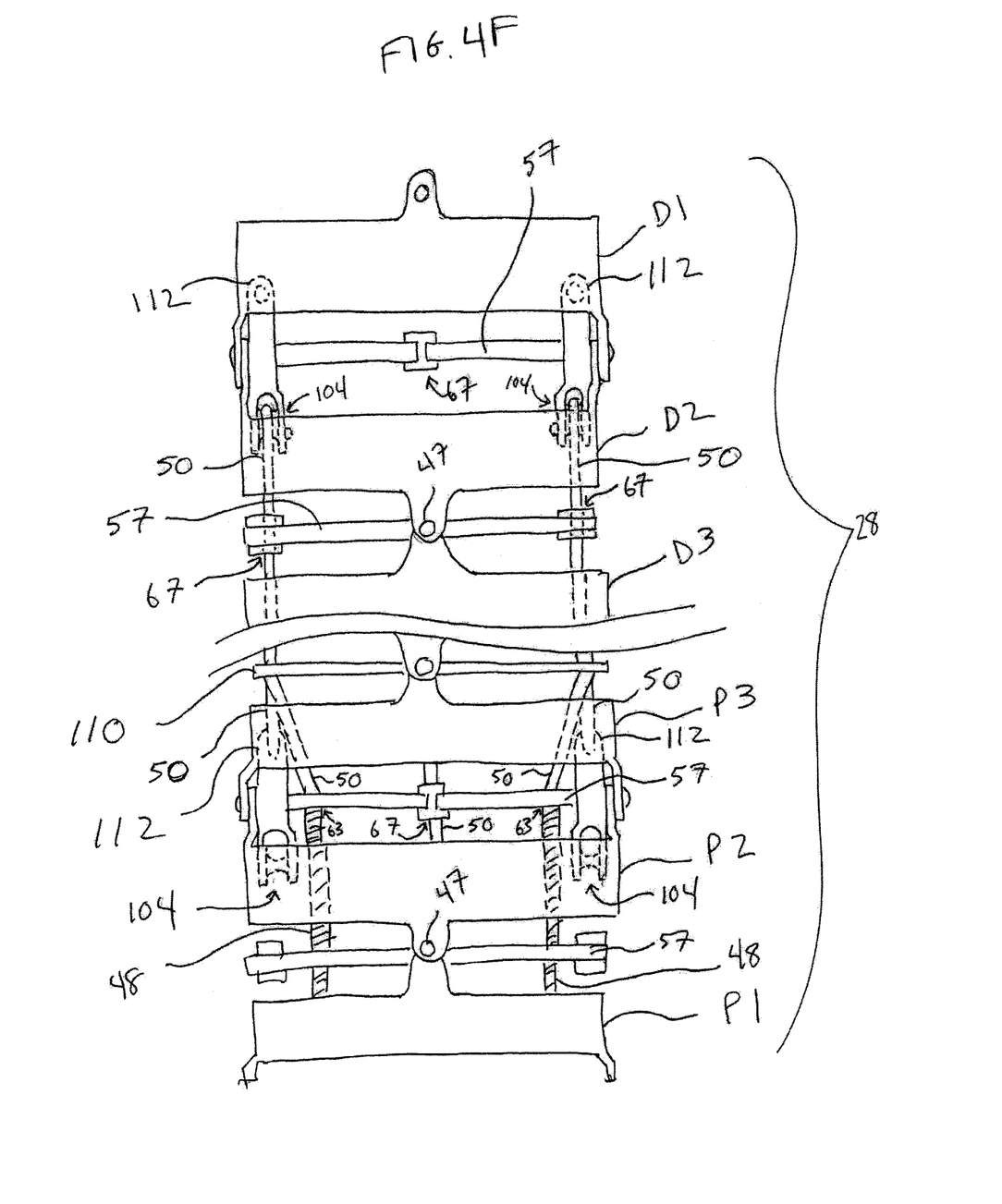
FIG. 4F illustrates an exemplary articulatable segment in accordance with the present invention.

FIG. 4F shows a side view of an articulatable segment 28, which includes the link shown in FIGS. 4D and 4E. Inner cross bar members 57 are shown hingedly coupled to and "between" links D1 and D2, P3 and P2, and P2 and P1. Coil pipes 48 are shown attached to holes 63 (shown in FIGS. 4D and 4E) of the inner cross bar member 57 disposed between links P2 and P3. Tendons 50 exit the coil pipes and extend distally from the inner cross bar member 57 and pass through peripheral holes in intermediate control ring 110. Intermediate control ring 110 helps maintain the position of the tendons towards the periphery and away from the inner lumens of the segment. The tendons then extend further distally until they engage force modifying elements 104, which are shown coupled to the inner bar cross member 57 that is disposed between links D1 and D2. It should be understood that the force modifying elements 104 that are coupled to the most distal inner cross bar member shown, while not disposed at the literal distal end of the segment, are considered to be at the "distal end" and/or "near the distal end" as these phrases may be used herein. Tendons 50 engage force modifying elements 104 and extend proximally from the force modifying elements 104 as the distal ends of tendon 50 are attached to tendon attachment points 112.

In one embodiment the tendon attachment point comprises a hole and tendons 50 are tied-off in the hole; in other more preferred embodiments the attachment point is a bar to which the tendon is tied or otherwise attached. The tendons can, however, be attached to tendon attachment points 112 by any attachment mechanism that will suit the purpose, such as an adhesive.

Holes 67 in the cross-bar are generally used to guide tendons axially along the segment, while holes 63 are generally used as the attachment locations for the coil pipes. Holes 63 are shown (In FIGS. 4D and 4E) to have a slightly smaller diameter than holes 67, although the size differentiation could be reversed or the sizes could be the same.

While not shown, it is understood that the segment 28 shown in FIG. 4F comprises a third and fourth coil pipe, which are offset by 90 degrees from the two coil pipes shown. These two additional coil pipes are attached to the holes 63 (not shown) of the inner cross bar member 57 between links P1 and P2. In the figure, one of the additional coil pipes is essentially "behind" joint 47 that hingedly couples P1 and P2 together, while the fourth coil pipe is offset 180 degrees from that coil pipe. It is, therefore, understood that two of the coil pipes (which are shown) are attached to the inner cross bar member between the second and third most proximal links (P2 and P3), while two of the coil pipes (those not shown) are attached to an inner cross bar member between the most proximal and second most proximal links (P1 and P2).

Similarly, the four force modifying elements (two of which are shown and two of which are not) assume similar relative positions. The tendons which extend from the coil pipes which are attached to the P2/P3 cross bar member engage and interact with the force modifying elements coupled to the cross bar member between the most distal and second most distal links (D1 and D2). The third and fourth tendons (not shown) which extend from the coil pipe which is attached to the P1/P2 inner bar cross member engage and interact with the force modifying elements (not shown) which are coupled to the cross bar member between the second and third most distal links (D2 and D3).

Therefore, in the embodiment shown in FIG. 4F, all four of the coil pipes do not attach to the same link, nor are all four force modifying elements coupled to the same link. The second pair (not shown) is located across from each other and at 90 degrees to the two coil pipes which are shown.

The position of the force modifying elements relative to the joints that hinge the links together can cause the segment to more efficiently articulate. As the tendon 50 shown to the left in FIG. 4F is actuated, the segment can more efficiently be articulated because as forces are applied along the path of the tendon (in response to the actuation force), the segment articulates more efficiently at joint 47, as D2 bends towards the left of the page relative to D3, because the force modifying element enhances the force applied across the segment. Joint 47 that connects D2 and D3 is offset 90 degrees from the force modifying element.

The skilled artisan will appreciate that all the coil pipe-tendon-force modifying combinations may be located on a single cross-bar or on a single link, rather than adjacent links or adjacent cross-bars, as in the depicted embodiment. Additionally, the skilled artisan will recognize that use of four combinations is a preferred embodiment, and that more or fewer may be used to achieve the desired purpose.

It is understood that the cross-bar members of the segment can be considered to be a part of either of the two links to which it is hingedly coupled, or a separate element altogether. For example, when referring to force modifying element 104 disposed on cross bar member 57, it may be understood that either of the adjacent links comprises the force modifying element.

In preferred embodiments the distal end of the tendon is attached to the link to which the coil tube that houses that tendon is terminated. For example, as shown in FIG. 4F, tendons 50 are shown extending from the cross bar member 57 of the P2/P3 links, and tendons 50 are attached to tendon attachment points 112 of the same cross bar member 57. This will likely create the greatest amount of articulating force along the segment when the tendon is actuated. It should be appreciated, however, that the distal end of the tendon need not attach to the same link or the location to which the coil tube which houses that tendon is terminated. After engaging the force modifying element, the tendon can be coupled to any of the links proximal to the force modifying element, and preferably to the link of the coil tube termination. However, it should be noted that attachment of the tendon to links distal of the link where the coil tube terminates may change or alter the amount or distribution of force along the segment and concomitantly reduce the effectiveness of the force modifying element. The coil pipe does not need to be attached to the most proximal link (or the second most proximal link) in the segment. While the forces and distribution of forces generated along the segment may be altered along a segment by such an arrangement, it is not intended to be a limitation.

Similarly, the force modifying element(s) does not need to be coupled to either of the two most distal links. The advantage arises from attaching the distal end of tendon 50 to a location proximal to the force modifying element.

In the embodiment in FIG. 4F, the two most proximal links P1 and P2 of segment 28 serve as the two most distal links for a segment disposed proximally and adjacently to the segment shown in FIG. 4F (not shown). Force modifying elements 104 coupled to the cross bar member 57 of the P2/P3 link will engage and interact with tendons (not shown) that are used to articulate the adjacent proximal segment. The force modifying elements are coupled to the tendon attachment points in the preferred embodiment, although this is not intended as a limitation. The force modifying element engages and interacts with a tendon used to articulate a given segment, but the tendon attachment point coupled to that force modifying element is coupled to the distal end of a different tendon used to articulate an adjacent distal segment. Similarly, links D1 and D2 shown in FIG. 4F can serve as the two most proximal links of an adjacent distal segment (unless, of course, segment 28 in FIG. 4F is the distal most steering segment 14).

Again, while cross bar members 57 have been described as hingedly coupled to the links, they can be rigidly attached thereto, or they, or their components, can be integral with either one or both of the links. For example, the tendon attachment point and/or the force modifying element can be integral with a body 66 of link 64.

Figure 6A:
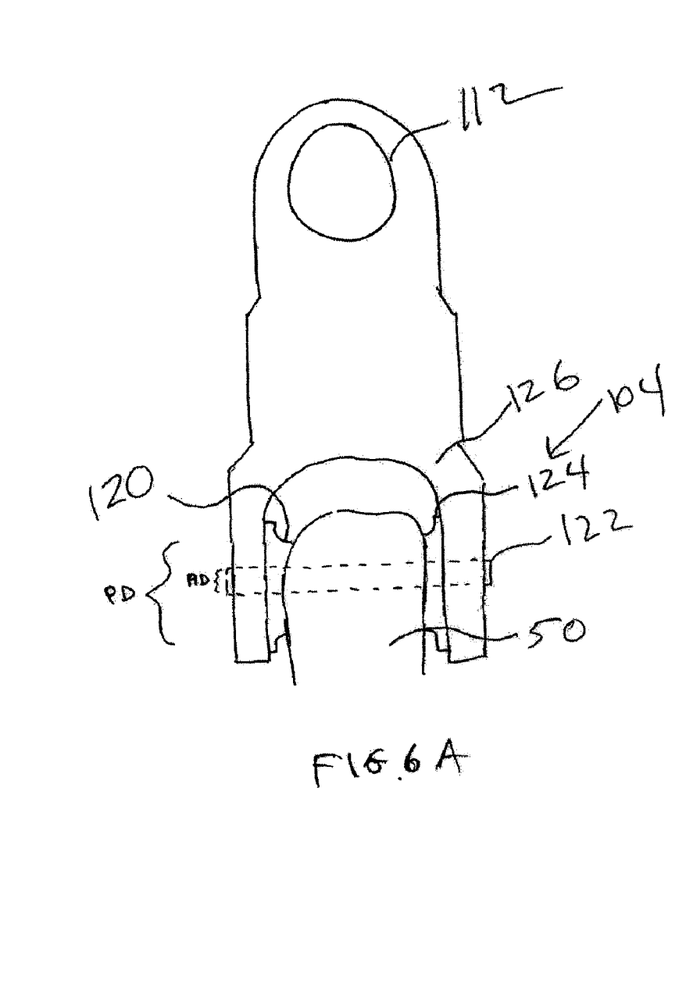
FIGS. 6A-6B illustrate front and side views on an exemplary force modifying element.
Figure 6B:
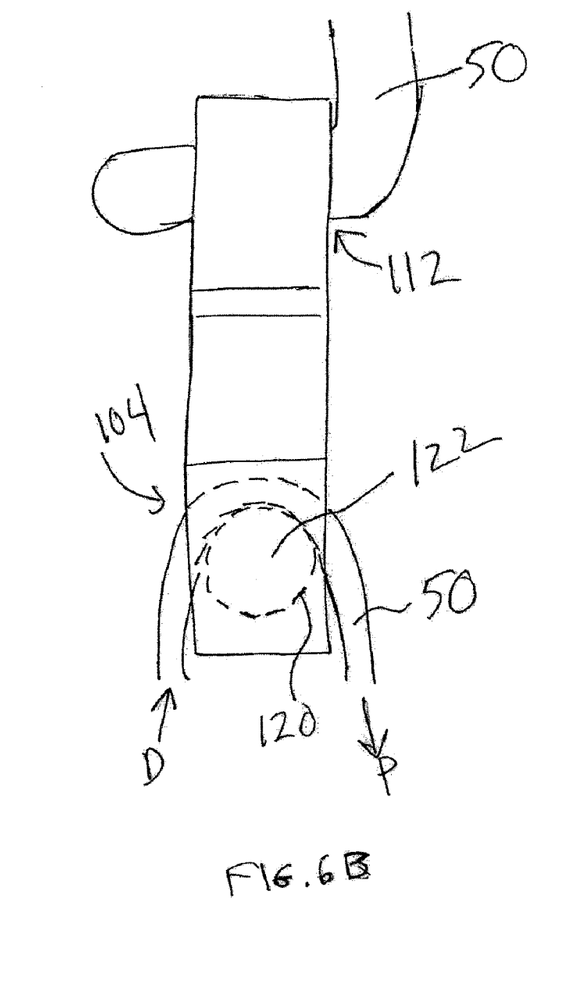

The force modifying elements 104 as shown in FIGS. 4D-4F are shown comprising curved surfaces with which the tendons 50 engage and interact. As shown, the tendons pass over the force modifying element, engaging with their curved surfaces. FIGS. 6A and 6B show a more detailed front and side views of the force modifying elements 104 shown in FIGS. 4D-4F, which include curved surface 120 and pin 122 (as shown, the force modifying element is also coupled to and integral with tendon attachment point 112 described above). FIG. 6B also shows a second tendon 50 attached to tendon attachment point 112 which would be used to articulate the adjacent distal segment.

Tendon 50 as shown engages and can slidingly interact with force modifying element 104 such that when the tendon is actuated (such as with a proximally-directed tensioning force) tendon 50 slides over curved surface 120 (in the direction as indicated by the arrows in FIG. 5B) as the segment articulates as described herein. In this embodiment the curved surface does not rotate, and the frictional forces between the sliding tendon and the curved surface 120 are minimized as much as possible. This will ensure that the largest articulating force possible is applied to the segment (to articulate the segment), as well as to minimize wear on the tendon. In this preferred embodiment, the tendon comprises polyethylene, which should smoothly slide over curved surface 120. It will be appreciated that curved surface 120 and pin 122 can have the configuration of a pulley, but it is not intended to be limited to a pulley arrangement.

The force modifying element shown comprises curved surface 120. Curved surface 120 assumes a "saddle-like" configuration, with raised edges 124 which can reduce friction between the tendon and the force modifying element body 126. When the force modifying element comprises a fixed surface which does not rotate, the surface need not be limited to a curved, cylindrically-shaped surface as described. It can assume a variety of configurations which allow the tendon to engage and interact with the force modifying element. In addition, surface 120 of the force modifying element can be integral with the link body. For example, the force modifying element can simply comprise two holes in a link with a smooth surface therebetween, wherein the holes allow for the tendon to pass through and over the curved surface.

In an alternative embodiment, the force modifying element may be a curved pulley surface that rotates about a pin or axel. The tendon will apply a force to the curved surface and also to the pin 122 when the tendon is actuated. When working with a system with small components, the size and materials of the force modifying element can be important to prevent deformation of the materials when relatively large forces are applied to them. For example, the axel diameter "AD", relative to the pulley diameter "PD", as well as the materials for each, are important in order to prevent catastrophic degradation of either the pulley or the axel as a result of the loads placed on each.

In a preferred embodiment, PD is 0.15 inches and AD is 0.04 inches, and the pin is comprised of a stainless type of alloy (preferably 416 family) and the working surface is comprised of a polymer such as polyetheretherketone (PEEK).

While the force modifying element has been described comprising a fixed smooth surface that slidingly interacts with a tendon, the force modifying element can be a variety of structures that create an increased amount of force applied to the articulatable segment to cause the segment to bend relative to one another. For example, the force modifying element can comprise a pulley, an axially moveable pulley, a plurality of such pulleys, a fixed ferrule, or other similar devices.

Referring again to FIG. 5, coil pipes 48 are fixed at their proximal and distal ends between actuator 60 and the proximal end of segment 28. When tendons 50 are placed under tension by actuation, the force is transferred across the length of segment 28; coil pipes 48 provide the opposite force at the proximal end of the segment being articulated in order to cause the articulation. This force is, primarily, a compression force or axial loading transferred along the length of the coil pipe. The force modifying element provides a mechanical advantage which results in a larger articulating force than would have existed but for the force modifying element. Theoretically, if 1 unit of force is imparted to the tendon by the actuator, 2 units of articulating force will be delivered. There will be some frictional losses, and therefore the ratio will not likely be as high as 2:1. The articulating force will, however, be larger than without the force modifying element. And even though the system is adapted to generate a theoretical 2:1 ratio force reduction, the system could obviously be adapted to have theoretical ratios different than 2:1, depending on the number and type of force modifying elements in each of the segments. For example, a plurality of pulleys could be used to generate a 4:1 mechanical advantage.

In some embodiments, the plurality of links are adapted such that when an actuation or tensioning force is applied to the segment the links do not become locked in position relative to an adjacent link (i.e., such that the links can not move relative to one another). In these embodiments the segment can therefore continue to articulate, or bend, as additional actuation, or tensioning, forces are applied to the segment. Although articulation of the segment may cause a link to come into contact with an adjacent link or to be temporarily fixed in place relative to an adjacent link, the links are adapted to be able to continue to move relative to one another (i.e., the segment can continue to be articulated) as additional tensioning forces are applied to articulate the segment. For example, FIG. 5 shows some of the links in segment 28 in contact with an adjacent link. Each link is not, however, in a locked position relative to an adjacent link. A link may continue to move relative to an adjacent link if a tensioning force is applied to the segment by one of the other tendons. Therefore, as additional tensioning forces are applied to the segment, the segment can continue to articulate.

A preferred embodiment of the present invention utilizes one actuator per tendon, and utilizes four tendons per segment, as described above. Details relating to actuator 60 and connecting actuator 60 to tendons 50 are described in U.S. patent application Ser. No. 10/988,212, incorporated herein by reference.

While the system has been described as an endoscope, it should be understood that the invention can be used in a wide variety of surgical tools and instruments used in a wide variety of treatments and procedures. Such devices may be used for a variety of different diagnostic and interventional procedures, including colonoscopy, bronchoscopy, thoracoscopy, laparoscopy, video endoscopy, and natural orifice transluminal (gastric) endoscopic surgery, etc.

The foregoing description, for purposes of explanation, used some specific nomenclature to provide a thorough understanding of the invention. Nevertheless, the foregoing descriptions of the preferred embodiments of the present invention are presented for purposes of illustration and description and are not intended to be exhaustive or to limit the invention to the precise forms disclosed; obvious modification and variation are possible in view of the above teachings.

What is claimed is:

1. A system for modifying an articulating force on an articulatable elongate body deliverable within a body cavity, the system comprising:
    an elongate body comprising an articulatable segment, wherein the articulatable segment comprises
        a plurality of links having central apertures that collectively form an internal lumen of the segment, and
        a cross bar member coupled to at least one of the links and comprising at least one force modifying element, wherein the cross bar member is disposed within and extends transversely across the internal lumen;
    a coil pipe within the elongate body having a proximal end terminated outside of the elongate body and having a distal end terminated at a proximal portion of the segment; and
    a tendon disposed at least partially within the coil pipe, the tendon having a proximal end and a distal end, wherein the proximal end is coupled to an actuator outside of the elongate body, wherein the tendon interacts with the force modifying element, and wherein the distal end is coupled to a link proximal to the force modifying element.

2. The system of claim 1 wherein the force modifying element is disposed at a distal portion of the segment.

3. The system of claim 1 wherein the distal end of the tendon is coupled to a proximal portion of the segment.

4. The system of claim 1 wherein the coil pipe and the distal end of the tendon are coupled to the same link.

5. The system of claim 1 wherein the segment comprises a plurality of cross bar members, each cross bar member being coupled to a respective one of the plurality of links and comprising at least one force modifying element,
    and wherein the system comprises a plurality of tendons each coupled at their proximal ends to the actuator and disposed to interact with a respective force modifying element.

6. The system of claim 5 wherein the plurality of tendons is at least three tendons.

7. The system of claim 1 wherein the force modifying element comprises a curved surface and wherein the tendon and force modifying element slidingly interact.

8. The system of claim 7 wherein the curved surface is a fixed curved surface.

9. The system of claim 7 wherein the tendon loops around the curved surface.

10. The system of claim 1 wherein at least one link is adapted to move in response to an actuation force to control articulation without being locked in position relative to an adjacent link.

11. The system of claim 1, wherein adjacent links are articulably coupled to each other at joints.

12. The system of claim 11, wherein the cross bar member is axially disposed between two adjacent links and coupled to the joints of the adjacent links.

13. The system of claim 12, wherein the cross bar member is hingedly coupled to the joints of the adjacent links.

14. The system of claim 1, wherein the cross bar member is hingedly coupled to the at least one link.

15. The system of claim 1, wherein the cross bar member is fixedly coupled to the at least one link.

16. The system of claim 1, wherein the cross bar member is integral with the at least one link.

17. The system of claim 1, wherein the force modifying element comprises a tendon attachment structure.

18. The system of claim 1, wherein the system comprises a plurality of coil pipes and the plurality of links comprise a plurality of proximal links and a plurality of distal links, and
    wherein a first set of coil pipes is attached to a first cross bar member that is positioned between a first link and a second link of the proximal links, and a second set of coil pipes is attached to a second cross bar member that is positioned between the second link and a third link of the proximal links, and
    wherein the first set of coils pipes is offset 90 degrees from the second set of coil pipes.

19. The system of claim 18,
    wherein the system comprises a plurality of force modifying elements,
    wherein a first set of force modifying elements is coupled to a third cross bar member that is positioned between a first link and a second link of the distal links, and a second set of force modifying elements is coupled to a fourth cross bar member that is positioned between the second link and a third link of the distal links, and
    wherein the first set of force modifying elements is offset 90 degrees from the second set of force modifying elements.

20. The system of claim 19,
    wherein the system comprises a plurality of tendons,
    wherein a first set of tendons extends from the first set of coil pipes and interacts with the first set of force modifying elements, and
    wherein a second set of tendons extends from the second set of coil pipes and interacts with the second set of force modifying elements.

21. The system of claim 1, wherein the cross bar member comprises at least one hole through which the tendon is routed axially along the segment.

22. The system of claim 1, wherein the cross bar member comprises at least one hole, and wherein a coil pipe is coupled to the cross bar member at the at least one hole.

* * * * *